(12) United States Patent  
Porter et al.

(10) Patent No.: US 8,715,356 B2  
(45) Date of Patent: May 6, 2014

(54) PROSTHETIC HAVING A MODULAR SOFT TISSUE FIXATION MECHANISM

(75) Inventors: Joshua R. Porter, Winona Lake, IN (US); Nathan A. Winslow, Warsaw, IN (US); Jeffrey Kneisl, Charlotte, NC (US); John W. Sperling, Rochester, MN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 23 days.

(21) Appl. No.: 13/085,538

(22) Filed: Apr. 13, 2011

(65) Prior Publication Data

US 2012/0035733 A1 Feb. 9, 2012

Related U.S. Application Data

(60) Provisional application No. 61/323,666, filed on Apr. 13, 2010.

(51) Int. Cl.  
*A61F 2/40* (2006.01)

(52) U.S. Cl.  
USPC .................................... 623/19.14; 623/18.11

(58) Field of Classification Search  
CPC ..... A61F 2/0811; A61F 2/30767; A61F 2/08; A61F 2/22846; A61F 2/2875; A61F 2/30771; A61F 2002/0077; A61F 2002/0081; A61F 2220/0025  
USPC ............ 623/18.11, 20.15, 22.11, 20.35, 22.4, 623/23.15  
See application file for complete search history.

(56) References Cited

U.S. PATENT DOCUMENTS

| | | | | |
|---|---|---|---|---|
| 2,719,522 A * | 10/1955 | Hudack | .................... | 623/23.15 |
| 3,979,778 A * | 9/1976 | Stroot | ........................ | 623/19.12 |
| 4,186,448 A * | 2/1980 | Brekke | ........................ | 128/898 |
| 4,355,427 A * | 10/1982 | Schneider | ................. | 623/19.14 |
| 4,384,373 A * | 5/1983 | Sivash | ........................ | 623/23.45 |
| 4,714,475 A * | 12/1987 | Grundei et al. | ............ | 623/20.32 |
| 5,013,315 A * | 5/1991 | Barrows | ........................ | 606/71 |
| 5,032,130 A * | 7/1991 | Schelhas et al. | ........... | 623/22.42 |
| 5,084,051 A * | 1/1992 | Tormala et al. | .................. | 606/77 |
| 5,330,531 A * | 7/1994 | Capanna | .................... | 623/19.14 |
| 5,358,526 A * | 10/1994 | Tornier | ...................... | 623/19.14 |
| 5,380,328 A * | 1/1995 | Morgan | .......................... | 606/70 |
| D368,777 S * | 4/1996 | Goble et al. | ................. | D24/145 |
| D374,286 S * | 10/1996 | Goble et al. | ................. | D24/145 |
| 5,702,457 A * | 12/1997 | Walch et al. | ............... | 623/19.13 |
| 5,702,486 A * | 12/1997 | Craig et al. | ............... | 623/19.14 |
| 5,741,335 A * | 4/1998 | Gerber et al. | .............. | 623/19.13 |
| 5,944,758 A * | 8/1999 | Mansat et al. | .............. | 623/19.14 |
| 6,127,596 A * | 10/2000 | Brown et al. | .............. | 623/16.11 |
| 6,228,120 B1 * | 5/2001 | Leonard et al. | ............ | 623/19.12 |
| 6,283,999 B1 * | 9/2001 | Rockwood, Jr. | ............ | 623/19.12 |
| 6,294,041 B1 * | 9/2001 | Boyce et al. | ................. | 156/275.5 |
| 6,350,284 B1 * | 2/2002 | Tormala et al. | ............ | 623/17.19 |
| 6,398,812 B1 * | 6/2002 | Masini | ........................ | 623/19.14 |
| 6,406,496 B1 * | 6/2002 | Ruter | .......................... | 623/19.14 |
| 6,520,994 B2 * | 2/2003 | Nogarin | ..................... | 623/19.14 |
| 6,558,425 B2 * | 5/2003 | Rockwood, Jr. | ........... | 623/19.12 |
| 6,592,622 B1 * | 7/2003 | Ferguson | ................... | 623/13.14 |
| 6,905,513 B1 * | 6/2005 | Metzger | ..................... | 623/20.17 |

(Continued)

*Primary Examiner* — Alvin Stewart  
(74) *Attorney, Agent, or Firm* — Harness, Dickey

(57) ABSTRACT

A method and apparatus for coupling soft tissue to a prosthetic is disclosed. Soft tissue attachment pads having porous metal attachment regions and suture accepting holes are selectively positioned onto an implantable prosthetic to provide coupling locations.

20 Claims, 9 Drawing Sheets

(56) References Cited

U.S. PATENT DOCUMENTS

| | | | |
|---|---|---|---|
| 7,001,429 B2* | 2/2006 | Ferguson | 623/13.14 |
| 7,070,622 B1* | 7/2006 | Brown et al. | 623/20.14 |
| 7,108,719 B2* | 9/2006 | Horber | 623/19.11 |
| 7,175,664 B1* | 2/2007 | Lakin | 623/19.14 |
| 7,241,486 B2* | 7/2007 | Pirhonen | 428/297.4 |
| 7,338,528 B2* | 3/2008 | Stone et al. | 623/19.14 |
| 7,462,197 B2* | 12/2008 | Tornier et al. | 623/19.13 |
| 7,507,256 B2* | 3/2009 | Heck et al. | 623/20.15 |
| 7,556,652 B2* | 7/2009 | Angibaud et al. | 623/19.14 |
| 7,615,080 B2* | 11/2009 | Ondrla | 623/19.11 |
| 7,753,963 B2* | 7/2010 | Boyer et al. | 623/23.63 |
| 7,875,082 B2* | 1/2011 | Naidu | 623/21.12 |
| 8,052,755 B2* | 11/2011 | Naidu | 623/21.12 |
| 8,100,982 B2* | 1/2012 | Heck et al. | 623/20.35 |
| 8,105,385 B2* | 1/2012 | Maroney et al. | 623/19.14 |
| 8,118,868 B2* | 2/2012 | May et al. | 623/13.14 |
| 8,177,849 B2* | 5/2012 | Meyers et al. | 623/20.32 |
| 8,182,542 B2* | 5/2012 | Ferko | 623/19.14 |
| 8,192,497 B2* | 6/2012 | Ondrla | 623/19.14 |
| 8,226,725 B2* | 7/2012 | Ferko | 623/20.14 |
| 8,460,393 B2* | 6/2013 | Smith et al. | 623/23.28 |
| 8,579,984 B2* | 11/2013 | Borowsky | 623/19.14 |
| 2003/0204267 A1* | 10/2003 | Hazebrouck et al. | 623/23.39 |
| 2005/0090902 A1* | 4/2005 | Masini | 623/19.14 |
| 2005/0177162 A1* | 8/2005 | McLeod et al. | 606/70 |
| 2005/0177241 A1* | 8/2005 | Angibaud et al. | 623/19.14 |
| 2005/0202371 A1* | 9/2005 | McGuire | 433/201.1 |
| 2006/0041317 A1* | 2/2006 | Hazebrouck et al. | 623/23.39 |
| 2006/0224242 A1* | 10/2006 | Swords et al. | 623/17.19 |
| 2007/0093835 A1* | 4/2007 | Orbay et al. | 606/69 |
| 2007/0244565 A1* | 10/2007 | Stchur | 623/19.14 |
| 2007/0270853 A1* | 11/2007 | Leung | 606/69 |
| 2008/0133024 A1* | 6/2008 | Meswania | 623/22.42 |
| 2008/0281428 A1* | 11/2008 | Meyers et al. | 623/20.35 |
| 2009/0216270 A1* | 8/2009 | Humphrey | 606/232 |
| 2009/0254189 A1* | 10/2009 | Scheker | 623/21.11 |
| 2009/0270860 A1* | 10/2009 | Bergin et al. | 606/62 |
| 2009/0317447 A1* | 12/2009 | Hsiao et al. | 424/426 |
| 2010/0076570 A1* | 3/2010 | Band et al. | 623/23.12 |
| 2010/0312284 A1* | 12/2010 | Linares | 606/286 |
| 2011/0009973 A1* | 1/2011 | Meyers et al. | 623/20.32 |
| 2011/0130840 A1* | 6/2011 | Oskouei | 623/18.11 |
| 2011/0144762 A1* | 6/2011 | Bergin et al. | 623/23.44 |
| 2011/0213467 A1* | 9/2011 | Lozier et al. | 623/20.32 |
| 2011/0251698 A1* | 10/2011 | Gupta et al. | 623/23.56 |
| 2011/0313532 A1* | 12/2011 | Hunt | 623/18.11 |
| 2012/0109166 A1* | 5/2012 | Melvin et al. | 606/151 |
| 2012/0158136 A1* | 6/2012 | Voisard et al. | 623/11.11 |
| 2012/0303061 A1* | 11/2012 | Bhatnagar et al. | 606/246 |
| 2013/0030529 A1* | 1/2013 | Hunt | 623/16.11 |
| 2013/0090733 A1* | 4/2013 | Kraft et al. | 623/17.16 |
| 2013/0268084 A1* | 10/2013 | McMinn | 623/22.32 |
| 2013/0304218 A1* | 11/2013 | Ullrich et al. | 623/18.11 |
| 2013/0304227 A1* | 11/2013 | Hawkins | 623/23.5 |

* cited by examiner

PROSTHETIC HAVING A MODULAR SOFT TISSUE FIXATION MECHANISM

CROSS-REFERENCE TO RELATED APPLICATIONS

This application claims the benefit of U.S. Provisional Application No. 61/323,666, filed on Apr. 13, 2010. The entire disclosure of the above application is incorporated herein by reference.

FIELD

This invention relates generally to a method and apparatus for use in orthopedic surgery and, more particularly, to a method and apparatus for providing a prosthesis having a modular soft tissue coupling mechanism. The soft tissue coupling mechanism is a member configured to be optionally and selectively coupled to the implant and includes a fixation flange and porous metal portion, both of which are configured of being coupled to soft tissues.

BACKGROUND

It is generally known in the art to provide prostheses that replace or reinforce various portions of bone during an orthopedic surgical procedure. However, the current prior art prostheses along with the associated surgical components and instruments utilized during orthopedic surgery may suffer from many disadvantages.

For example, because the extent of degradation is not always evident until during the surgery, extensive bone resection may be necessary. Additionally, etiologies such as bone tumors or those requiring revision of an implanted joint require significant bone removal which may remove soft tissue fixation sites. In these cases, soft tissue fixation to the prosthesis may or may not be necessary. To provide for soft tissue attachment, some replacement joint components provide an integral flange configured to accept soft tissue attached to a lateral surface of the prosthetic replacement joint head. These fixed fixation flanges, however, may not provide the proper locational adaptivity needed during the orthopedic surgical procedure and leave the surgeon with little flexibility or no options as to soft tissue attachment.

An example of an orthopedic transplant is a shoulder prosthesis which typically comprises a humeral component and a glenoid component. The humeral component and the glenoid component are designed to be surgically attached to the distal end of the humerus and the scapula, respectively. The humeral component is further designed to cooperate with the scapula component in simulating the articulating motion of an anatomical shoulder joint.

Motion of a natural shoulder is kinematically complex. During a relatively broad range of flexion and extension, the articular or bearing surfaces of a natural shoulder experience rotation, medial and lateral angulation, translation, rollback and sliding. Shoulder joint prostheses, in combination with ligaments and muscles, attempt to duplicate this natural shoulder motion, as well as absorb and control forces generated during the range of motion. Depending on the degree of damage or deterioration of the shoulder tendons and ligaments, however, it may be necessary for a shoulder joint prosthesis to eliminate one or more of these motions in order to provide adequate stability.

What is needed then is a prosthesis and associated surgical components for use in orthopedic surgery which does not suffer from the above-mentioned disadvantages. This in turn, will provide a prosthesis which is stable and secure and increases the overall flexibility for a surgeon to fix soft tissues. It is, therefore, an object of the present invention to provide such a prosthesis and associated surgical components for use in orthopedic surgery.

SUMMARY

This section provides a general summary of the disclosure, and is not a comprehensive disclosure of its full scope or all of its features.

In accordance with the present teachings, an apparatus and method for providing a prosthetic having a modular soft tissue attachment mechanism is disclosed. The apparatus and method employ modular soft tissue attachment mechanisms having porous metal pads for use during the orthopedic surgical procedure.

In one embodiment, an orthopedic implant has a body that is at least partially implantable within a bone. A mechanism for coupling soft tissue to the body is provided. The mechanism for coupling soft tissue to the body has an attachment member operable to prevent movement of the coupling mechanism with respect to the body. The mechanism defines a suture accepting aperture configured to couple soft tissue to the mechanism and has a porous soft tissue engaging surface.

A method for implanting a shoulder prosthetic is further disclosed. The method includes selecting an appropriately sized prosthetic component. Next, a determination is made if soft tissue fixation to the implant is necessary. Should it be necessary to couple soft tissue to the implant, a soft tissue fixation having a porous metal component is attached to the implant. The implant is subsequently implanted. Soft tissue is positioned adjacent to the porous metal component and allowed to grow into the porous metal component.

Use of the present teachings provides an apparatus and method for providing a prosthetic having a modular soft tissue attachment mechanism for use during an orthopedic surgical procedure. As a result, the aforementioned disadvantages associated with the currently available prostheses and associated surgical components have been substantially reduced or eliminated.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1B:
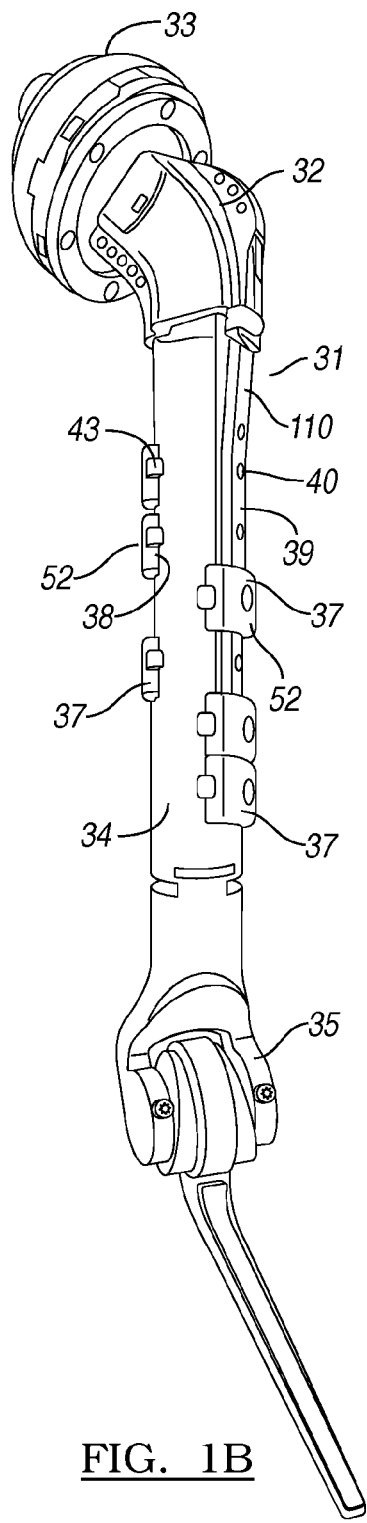
FIGS. 1A and 1B are an assembled view of the prosthetic component according to the teachings of one embodiment.
Figure 1A:
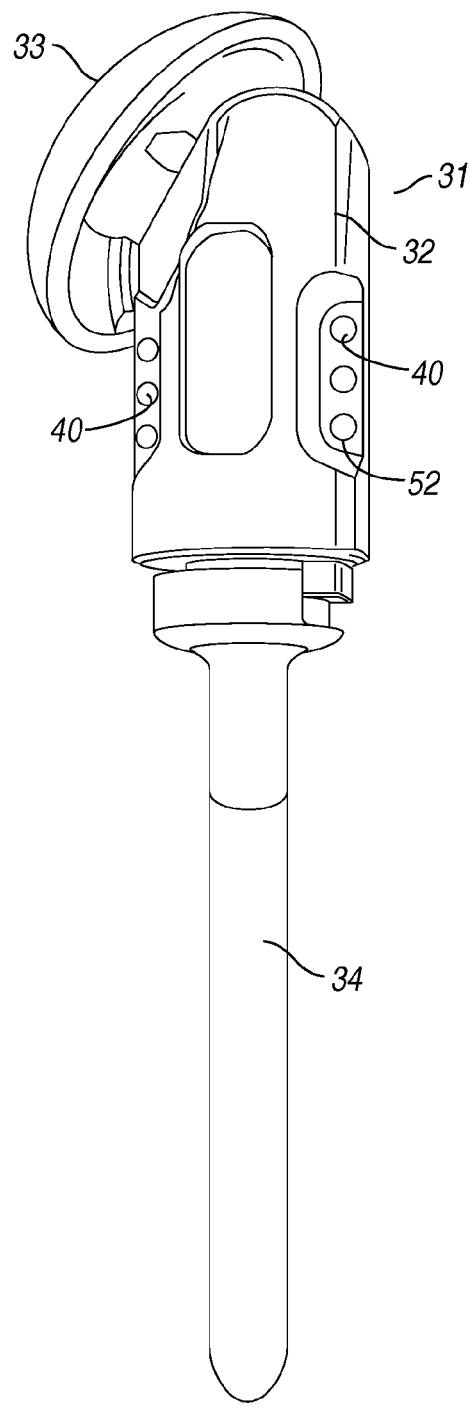

Example embodiments will now be described more fully with reference to the accompanying drawings. FIGS. 1A and 1B represent components used in a shoulder arthroplasty according to the present teachings. As shown, a modular humeral component 31 has a base member 32, and a head member 33 having an articulating bearing surface. Optionally, the modular humeral component 31 can have a fixation stem 34 (see FIG. 1A) or an elbow prosthesis 35 (see FIG. 1B).

The base member 32 is configured to be coupled to the fixation stem 34 and head 33 using coupling tapers (not shown). The fixation stem 34 can be used to attach the modular humeral component 31 to a resected bone of the humerus.

If a total humeral replacement is being conducted, the modular humeral component 31 shown in FIG. 1B can be used. The elbow prosthesis 35 can be coupled to a fixation stem 34 using locking tapers or other suitable coupling mechanism.

Attached to the modular humeral component 31 is a plurality of modular soft tissue attachment pads 37. The soft tissue attachment pads 37 have a coupling surface 38 which is configured to be selectively coupled to a coupling surface 39 on the modular humeral component 31. In this regard, the modular humeral component 31 has a plurality of apertures 40 defined at various locations on the surface of the modular humeral component 31 therein. The apertures 40 are configured to accept coupling fasteners which are configured to couple the soft tissue attachment pads 37 to specific locations on the modular humeral component 31.

The soft tissue attachment pads 37 function as soft tissue coupling locations. In this regard, the soft tissue attachment pads 37 define a bore 43 configured to accept a suture engaged with soft tissue such as a tendon, ligament or muscle. In practice, after the modular humeral component 31 is coupled to the patient, soft tissue is coupled to the soft tissue attachment pads 37 by passing the suture through the soft tissue and passing the suture through the bore 43. The soft tissue can then be positioned so that the soft tissue is in contact with a porous metal surface. The soft tissue then grows into the porous metal surface, aiding in fixation.

Figure 2:
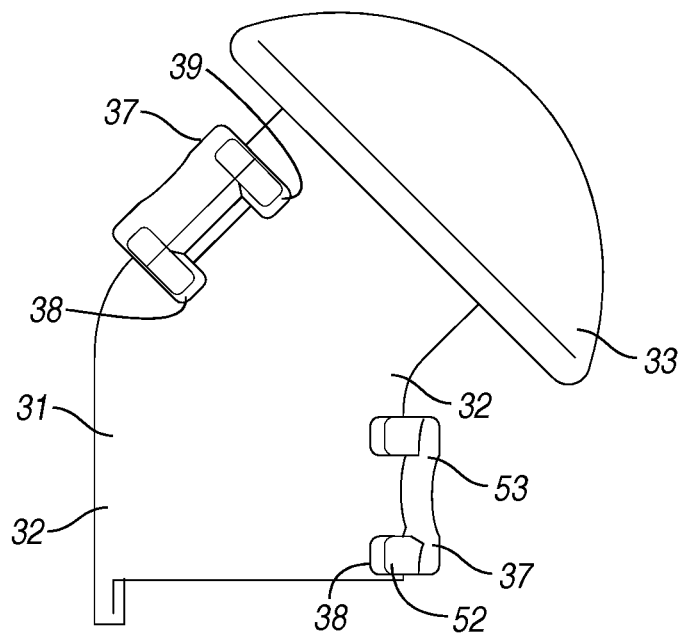
FIG. 2 is a side view of an alternate base humeral component with humeral head according to the present teachings.
Figure 3:
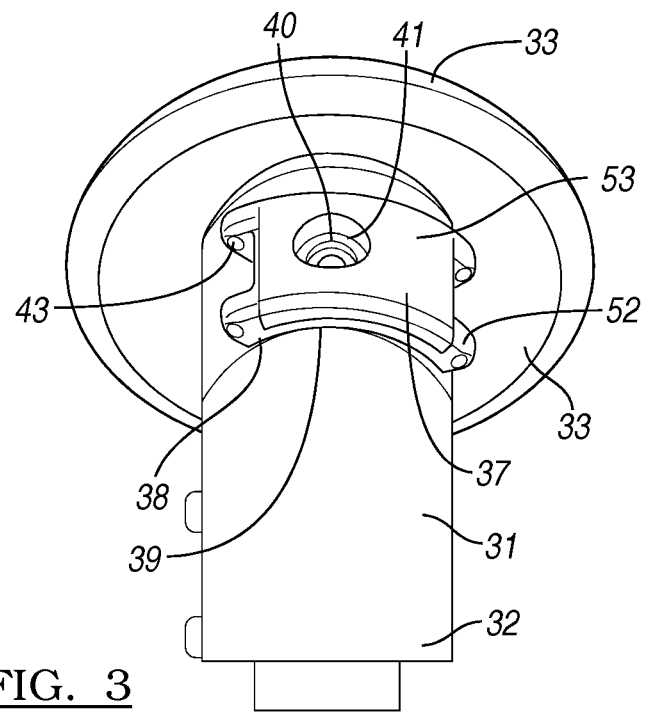
FIG. 3 represents an alternate view of the humeral component shown in FIG. 2 according to the present teachings.
Figure 4:
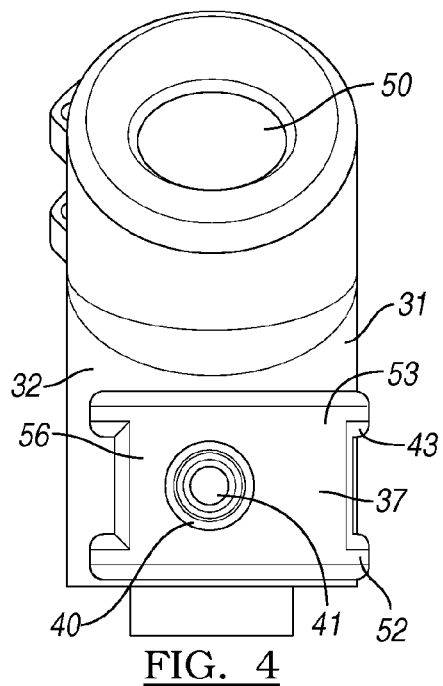
FIG. 4 represents a soft tissue fixation member coupled to the humeral component of the present teachings.

FIGS. 2-4 represent the base member 32 having associated soft tissue attachment pads 37. As shown in FIG. 3, soft tissue attachment pads 37 define a fastener accepting through bore 41. The through bore 41 is configured to be aligned with a bore 40 defined in the base member 32.

Figure 5:
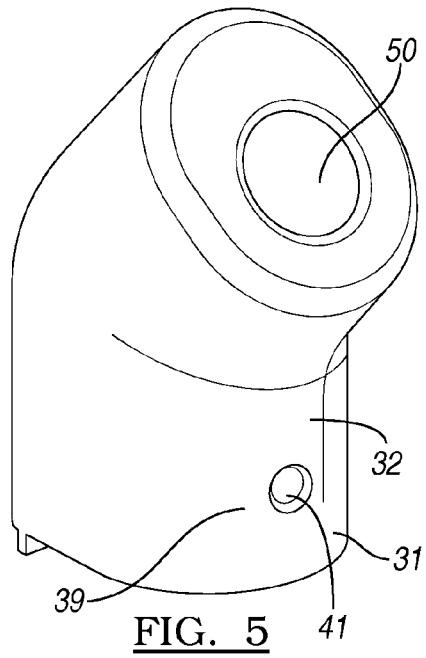
FIGS. 5-7 represent perspective, side and rear views of a prosthetic according to the present teachings.
Figure 6:
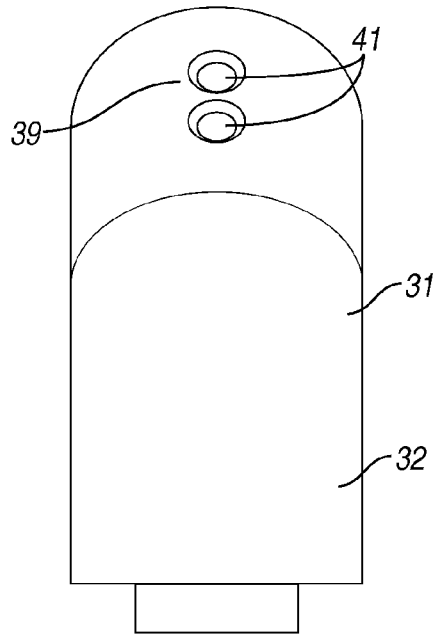
Figure 7:
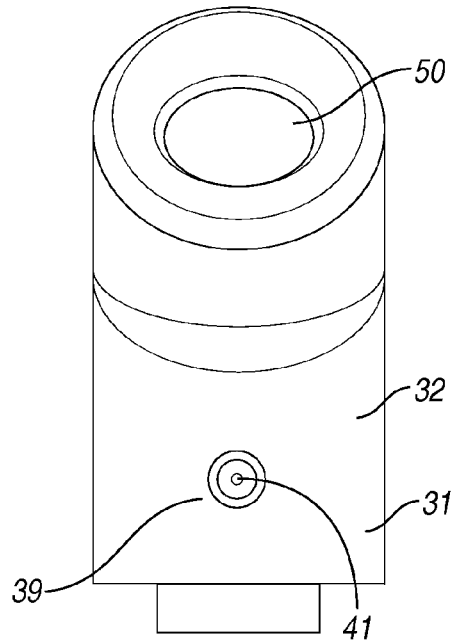

FIGS. 5-7 represent perspective, rear and front views of the base member 32. Defined in the base member 32 are coupling tapers 50 which are used to couple the base portion to the head or the fixation stem. Also defined in the base member 32 is a plurality of threaded fastener accepting bores 41. These fastener accepting bores 41 can be generally located at soft tissue accepting locations. It is, of course, envisioned that a physician may need to fix soft tissue to non-traditional locations due to damage to the soft tissue.

Figure 8A:
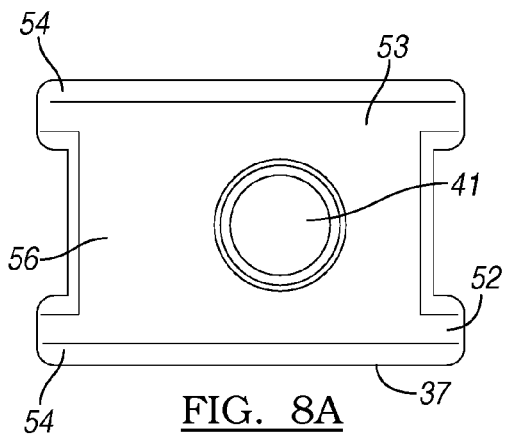
FIGS. 8A-8C represent the top, end and side views of a soft tissue fixation member according to the present teachings.
Figure 8B:
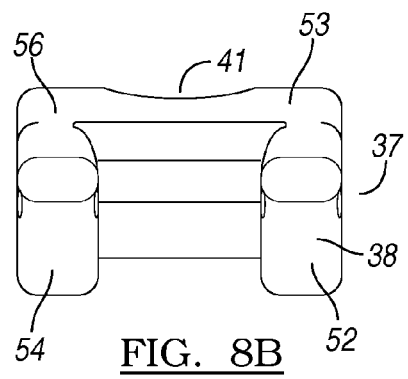
Figure 8C:
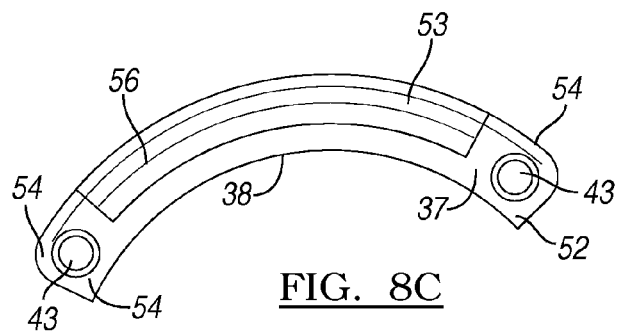

FIGS. 8A through 8C represent top, end and side views of the soft tissue attachment mechanism. The soft tissue attachment pads 37 have a plate 52 made of a biocompatible material such as titanium. Disposed on the plate is a pad of porous metal material 53 such as Regenerex. Defined through the porous metal pad 56 and plate 52 is the fastener accepting aperture.

As best seen in FIG. 8C, disposed on proximal and distal ends are a pair of flanges 54 which define suture accepting bores 43. In use, a suture is passed through soft tissue and then passed through the suture accepting bore 43 of the pair of flanges 54. The suture accepting bores 43 are shown as being generally parallel to the center of curvature "C" of the coupling surface 38 of the soft tissue attachment pads 37. As described below, the suture accepting bores can be parallel to, skew or perpendicular to the coupling surface 38.

Figure 9:
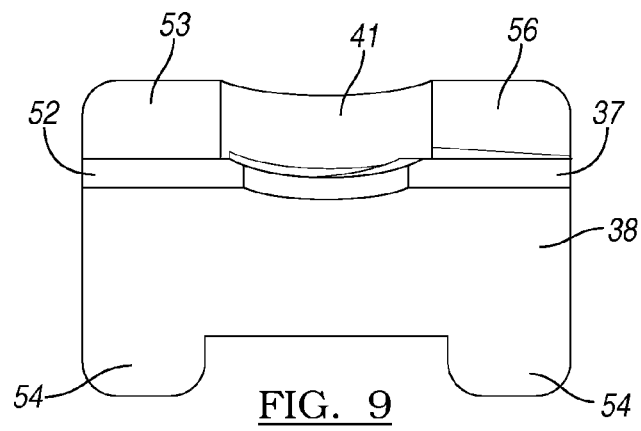
FIG. 9 represents a sectional view of the soft tissue coupling member of FIGS. 8A-8C.

FIG. 9 represents a cross-sectional view of the soft tissue attachment pads 37. Shown is the plate 52 having the coupling surface 38 configured to mate against an implant or bone. Also shown is the porous metal pad 56 which functions as a site for ingrowth of the soft tissue.

Figure 10A:
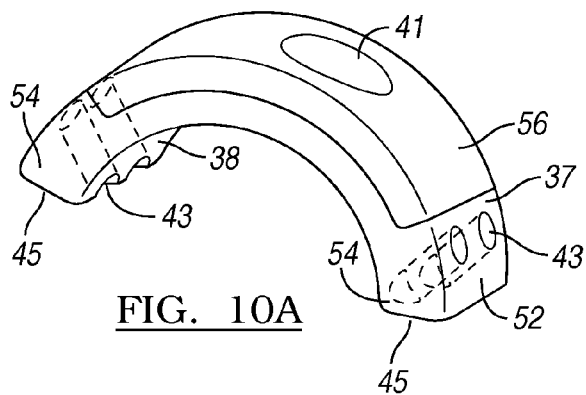
FIGS. 10A and 10B represent soft tissue coupling mechanisms according to the present teachings.
Figure 10B:
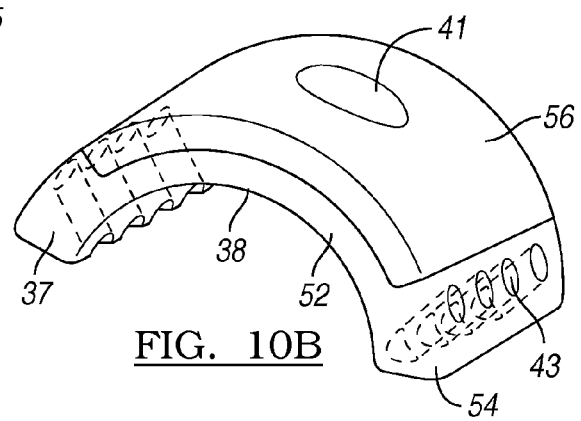

FIGS. 10A and 10B represent alternate soft tissue attachment pads 37. As shown, the plate 52 can have varying axial lengths. Additionally shown is an alternate configuration for the suture accepting bores 43. The fastener accepting bore 41 can be angularly adjusted in a non-centered manner from one of the terminal end 45 of the soft tissue attachment pad 37. The suture accepting bores 43 are aligned so that at least a portion of the bore is disposed on a terminal end 45 of the soft tissue attachment pad 37 or plate 52. This allows the treating physician to couple the soft tissue attachment pad 37 to the prosthetic after the coupling thereto.

Figure 11:
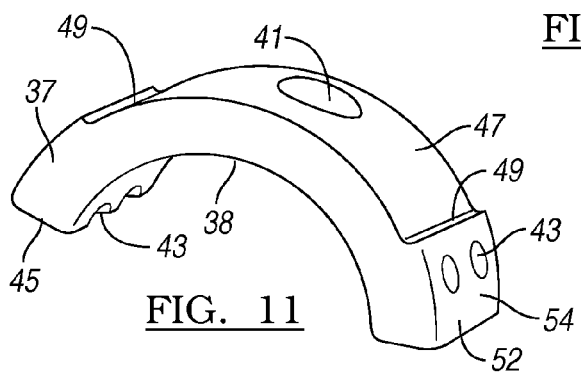
FIG. 11 represents a perspective view of the soft tissue coupling mechanism without the porous coupling member.

FIG. 11 represents the plate 52 for the soft tissue attachment pad 37. Shown is a notched surface 47 which is configured to accept the porous metal pad 56. Optionally, the notched surface 47 has a pair of terminal edges 49 which can define the depth of the porous metal pad 56. Porous metal pad 56 is a separate member which can be made of porous metal, porous coated metal or some biologic material. The porous metal pad 56 can be attached to plate 52 by cement, glue, weld, sintering, etc. Alternatively, the area defined by notched surface 47 can be filled with porous plasma spray. The metal pad 56 can have a porosity of about 70% and a pore size ranging from about 300-600 microns. This pore size can improve function in vivo. The open pores allow vascularization/angiogenesis and nutrient delivery which can be important for soft tissue in-growth or insertion. Traditional plasma spray is not thought to provide these benefits.

Figure 12:
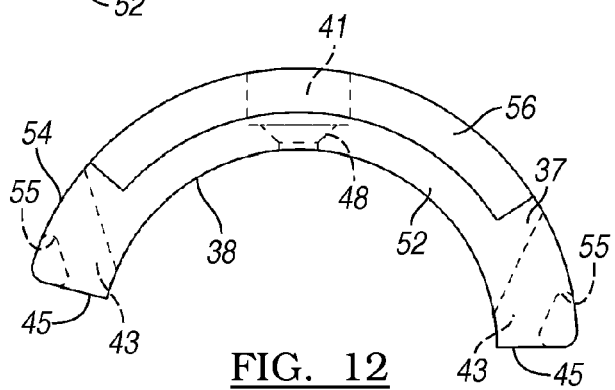
FIG. 12 represents a side view of the soft tissue coupling member of FIG. 10B.

FIG. 12 represents a side view of the plate 52 shown in FIG. 11. Shown in the plate 52 is the defined fastener accepting bore 41. The bore 41 has a first portion with a generally cylindrical cross-section. Optionally, a fastener bearing surface 48 can be defined in a second portion of the bore 41. Also shown is a cross-section of the suture accepting bore 43. The suture accepting bore 43 has a curved surface 55 which is configured to reduce the risk of breakage of the suture. The bores 43 are positioned in a way which located one end of the bore 43 on an exterior curved surface of the soft tissue attachment pad 37. The other end of the bore can be formed in the terminal ends 45 of the soft tissue attachment pads 37.

Figure 14:
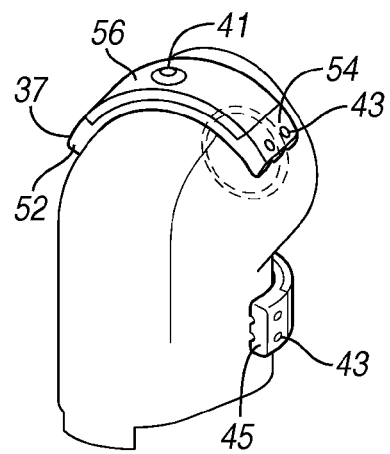
FIG. 14 represents a subassembly of soft tissue coupling mechanisms coupled to a head fixation member.
Figure 13:
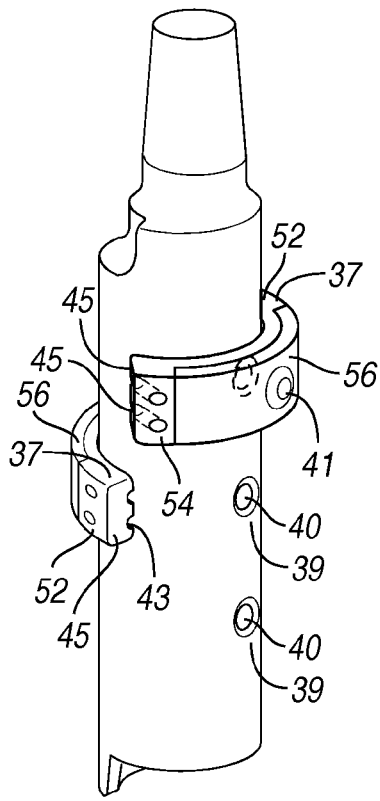
FIG. 13 represents the coupling of the soft tissue coupling mechanism to a prosthetic stem.
Figure 15:
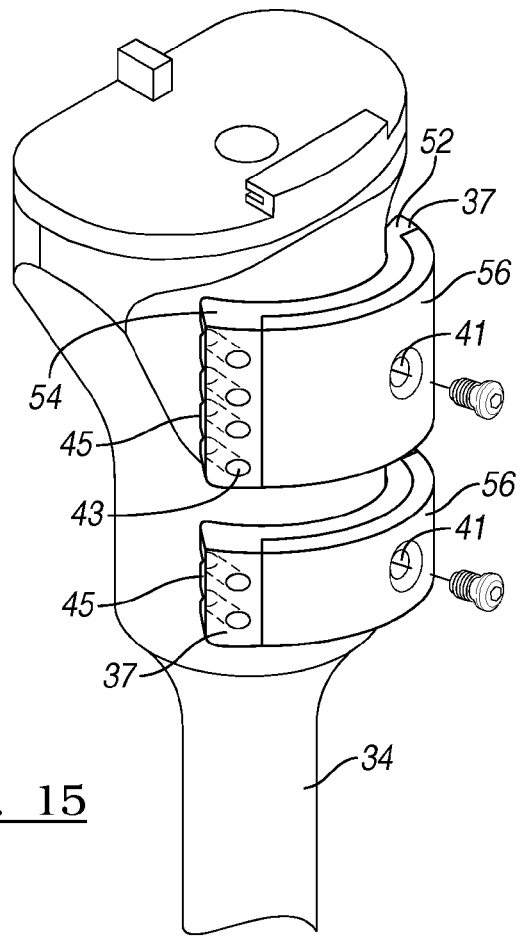
FIG. 15 represents the coupling of soft tissue coupling members to a femoral component.
Figure 16:
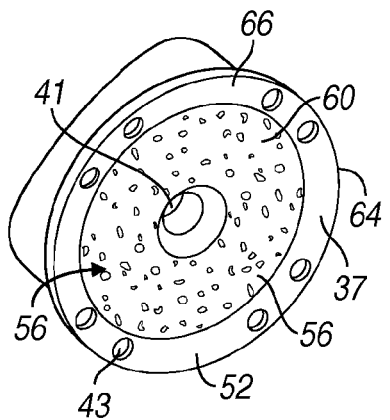
FIG. 16 represents an alternate soft tissue coupling member.

As shown in FIGS. 13-15, the soft tissue attachment pads 37 according to FIGS. 8A-12 can be coupled to various locations on disparate portions of monolithic or modular prosthetic systems depending upon the need of the treating physician. The soft tissue attachment pads 37 can have varying thicknesses of axial length depending upon the need of the patient.

Figure 17:
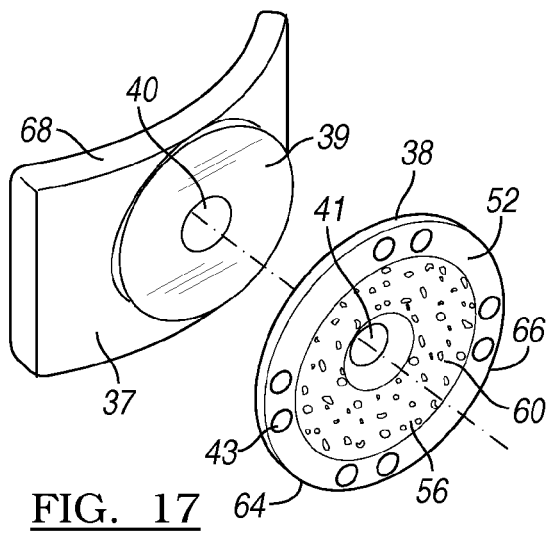
FIG. 17 represents an exploded view of the soft tissue coupling member being fixed to a coupling surface on a prosthetic.

FIGS. 16-21 represent an alternate soft tissue attachment pad 37. The soft tissue attachment pads 37 can have a generally planar yet circular configuration. A central portion 60 of the soft tissue attachment pads 37 can support the porous metal pad 56. Disposed about the periphery 64 of the soft tissue attachment pads 37 is a rim 66 defining the plurality of suture accepting bore 43. As shown in FIG. 17, the soft tissue attachment pad 37 has a planar coupling surface 38 which can be coupled to a curved intermediate member 68. The curved intermediate member 68 has a planar bearing or coupling surface 39 which mates with the planar coupling surface 38 on the soft tissue attachment pad 37. The curved intermediate member 68 has a curved surface configured to couple to a curved surface on the prosthetic.

Figure 18B:
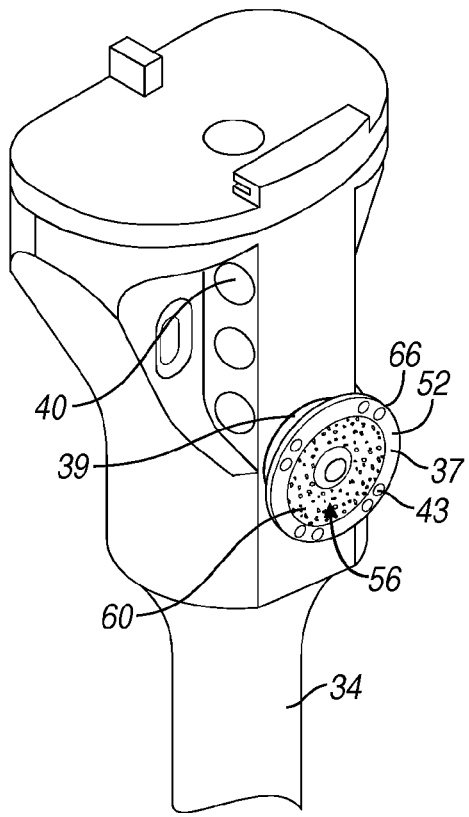
FIGS. 18A and 18B represent the coupling of the soft tissue coupling member according to FIG. 16 to a femoral prosthetic.
Figure 18A:
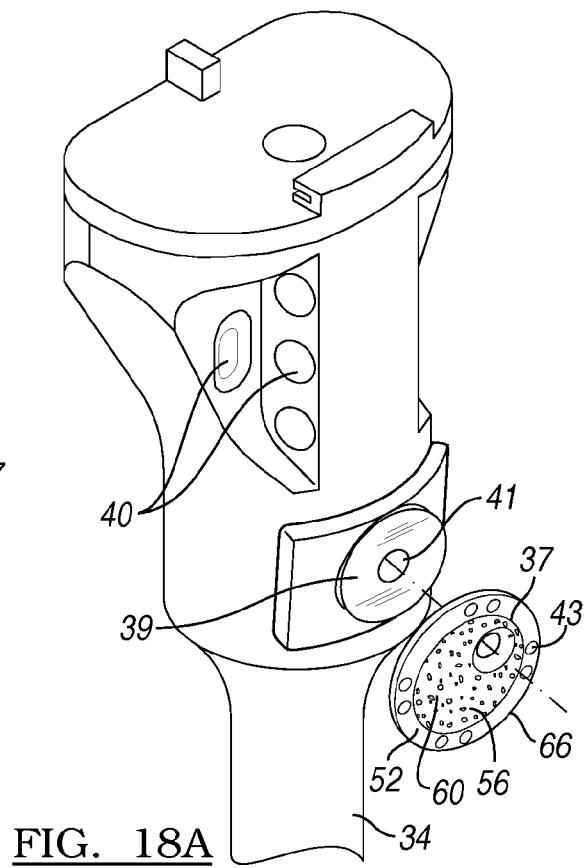

As shown in FIGS. 18A and 18B, the soft tissue attachment pad 37 can be coupled either to a planar or a curved surface. By rotation of the soft tissue attachment pad 37 about the fastener accepting bore 41, the location of the suture accepting bores 43 can be adjusted. By offsetting the bore 41, rotation of the soft tissue attachment pad 37 will translate the location of the suture accepting bores 43 with respect to the prosthetic.

Figures 19, 20, 21:
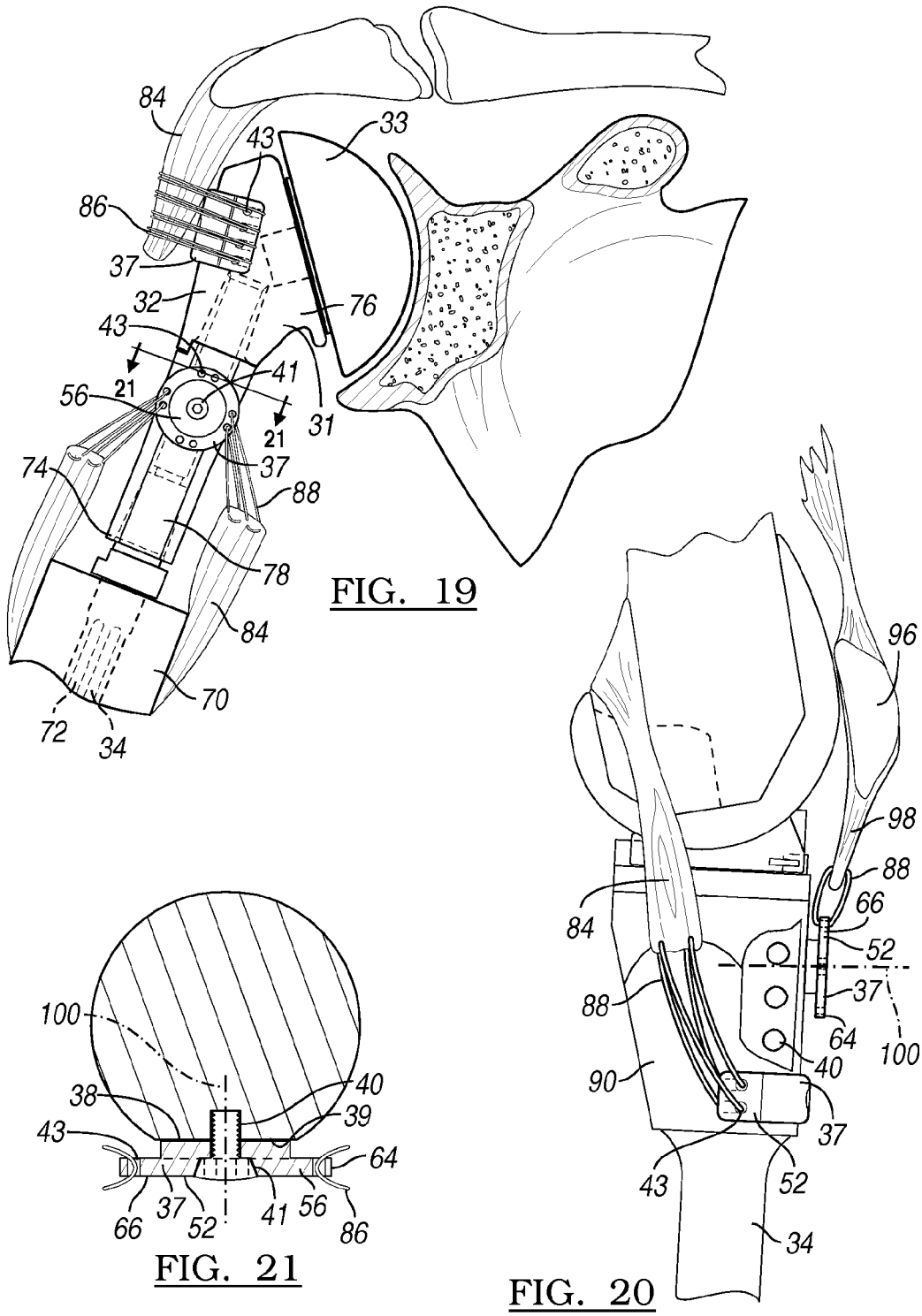
FIG. 19 represents an implanted view of the soft tissue coupling member according to FIG. 16 coupled to a humeral prosthetic.
FIG. 20 represents the use of the soft tissue coupling member on a femoral prosthetic.
FIG. 21 represent a cross-sectional view of the soft tissue coupling member coupled to the humeral stem of FIG. 19.

FIGS. 19 and 20 represent implanted prosthetics 70 and 90 according to the present teachings. As shown, both the soft tissue attachment pads according to FIGS. 1-10A and FIGS. 6 and 7 can be used with the same implant. FIG. 19 represents a humeral prosthetic 70 having a humeral fixation stem 72, an intermediate portion 74, a head coupling portion 76, and head 33. As is known, the portions of the implant can be coupled together using locking tapers 78. The use of the soft tissue attachment pads 76 allows for a treating physician to selectively attach soft tissue to various locations on the prosthetic 70. Optionally, in instances where the soft tissue is not an appropriate length due to degradation, the soft tissue can be coupled to the prosthetic at a location which does not represent the normal location of soft tissue attachment to the bone. Multiple sutures 86 can be used to hold soft tissue at a location adjacent to the porous metal portion of the soft tissue attachment pad 37. Optionally, the loops of sutures 88 can be arranged to couple the soft tissue 84 to the prosthetic 70.

FIG. 20 represents a femoral prosthetic 90 with associated soft tissue coupling pads according to the present teachings. Shown is the coupling of pads having both planar and curved coupling surfaces 38. After implantation of the prosthetic 90 into the resected femur 94, the soft tissue associated with the patella 96 can be coupled to the prosthetic 90. Depending on the amount of damage, the soft tissue 98 can be placed in direct contact with the soft tissue attachment pad 37 or can be disassociated and coupled with suture loops 88 or artificial graft material.

As briefly described above and shown in FIG. 21, the soft tissue attachment pads 37 can be rotatably positioned about an axis 100 generally disposed along the axis of the coupling bore 41. After implantation of the prosthetic 70, a treating physician can couple the soft tissue attachment pad 37 to the prosthetic 70 using a coupling mechanism such as a threaded fastener. It is envisioned the soft tissue attachment pads 37 can also be attached using other mechanism such as a locking taper, deformable flanges or translatable members.

Figure 22:
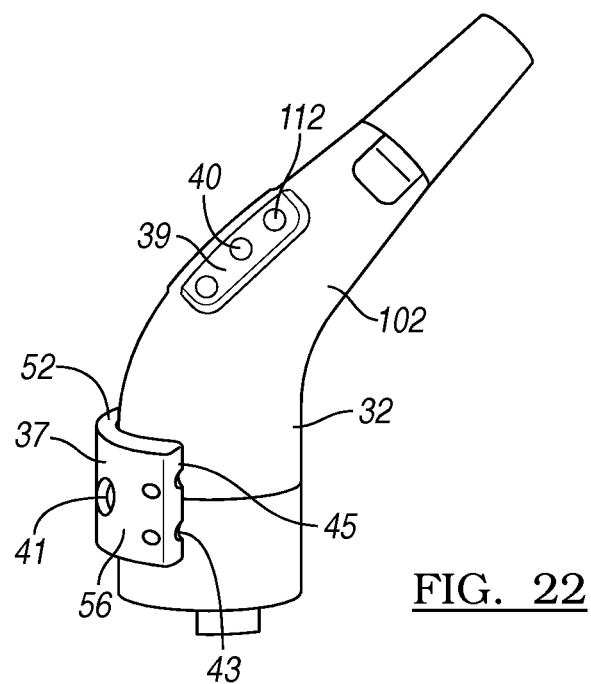
FIGS. 22 and 23 represent femoral head coupling members having soft tissue coupling mechanisms according to the present teachings.
Figure 23:
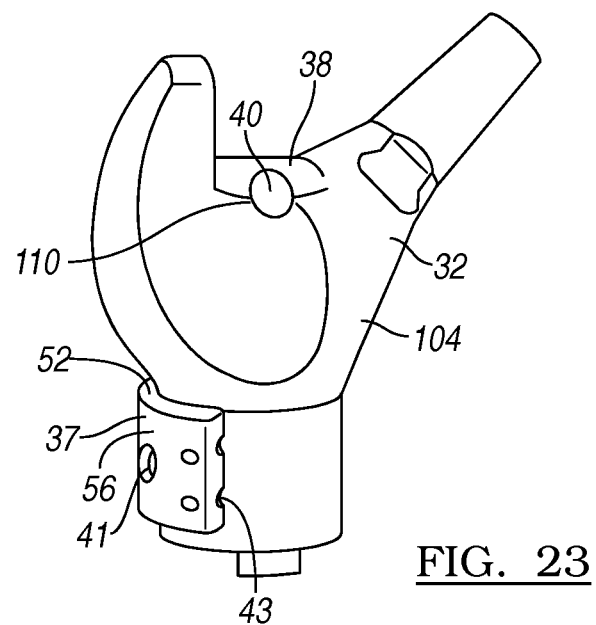

FIGS. 22 and 23 represent alternate components 102 and 104 of a prosthetic. These intermediate femoral members are shown to illustrate some of the various surfaces which can be utilized to couple the soft tissue attachment pads 37 to the prosthetic. In this regard, it is envisioned the soft tissue attachment pads 37 can be configured to be coupled to convex rail features 110 (see FIG. 1B), planar features (see FIG. 21) or concave channel features 112 (see FIG. 22). The variety of coupling surfaces 38, 39 and locations is intended to give the treating physician maximum flexibility in the operating theater.

While the soft tissue attachment pad 37 is shown throughout the application as a cylindrical surface disposed on an implant positioned within an intermedullary canal, it should be noted that the soft tissue fixation members can further take the form of a plate coupled to either a cylindrical or flat baseplate member. In this regard, the soft tissue fixation mechanisms can take the form of a plate member capable of accepting a suture or suture anchor. Additionally, the prosthetic need not be associated with a joint, e.g. an intercalary member.

Additionally, the soft tissue fixation mechanisms can be adjustably positioned on the prosthetic in one or more fixation areas. In this regard, multiple soft tissue fixation mechanisms can be located on multiple locations of a single implant. While the soft tissue fixation mechanisms is shown on a modular prosthetic, those skilled in the art will recognize that only the soft tissue fixation mechanisms need be modular and that the soft tissue fixation mechanisms can be fixed to any single piece prosthetic device. It is envisioned that a kit can be formed utilizing various sized prosthetic as well as various types and sizes of soft tissue coupling mechanisms.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The description of the invention is merely exemplary embodiments in the present invention. One skilled in the art would readily recognize from such discussion and from accompanying drawings and claims that various changes, modifications, variations may be made therein without the spirit and scope of the invention. For example, while the soft tissue fixation mechanisms are shown being coupled to a humeral, femoral, or tibial implant, the soft tissue fixation mechanism can equally be applied to other joint implants such as, but not limited to, knees and elbows, and for whole bone replacement.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An orthopedic implant comprising:
   an implant having an articulating surface and a bone attachment region forming a complete functional implant configured to be implanted into a patient; and
   a soft tissue attachment pad comprising a plate and a separate porous metal pad attached thereto, said plate defining a notched recess disposed between opposing proximal and distal flanges and configured to accept said porous metal pad, said soft tissue attachment pad defining a suture accepting bore configured to accept a suture engaged with soft tissue and said soft tissue attachment pad operable to be attached to said implant with a locking mechanism, said locking mechanism including a fastener disposed through a first fastener accepting bore defined in the soft tissue attachment pad and coupled to a second fastener accepting bore defined in the bone attachment region of the implant, wherein said locking mechanism is configured to prevent movement of the soft tissue attachment pad with respect to the implant and wherein said complete implant is configured to be implanted into the bone in a first functional configuration with the soft tissue attachment pad and in a second functional configuration without the soft tissue attachment pad.

2. The orthopedic implant according to claim 1 wherein the first fastener accepting bore is offset and non-centered with respect to the soft tissue attachment pad to allow selective positioning of the soft tissue attachment pad with respect to the implant.

3. The orthopedic implant according to claim 1 wherein at least one of the proximal and distal flanges defines the suture accepting bore therethrough.

4. The orthopedic implant according to claim 3 wherein the at least one flange defines a plurality of suture accepting bores.

5. The orthopedic implant according to claim 3 wherein said bone attachment region is an exterior cylindrical surface which defines an axis, said suture accepting bore being parallel to the axis.

6. The orthopedic implant according to claim 1 wherein the soft tissue attachment pad defines a perimeter having four sides, adjacent sides of the four sides intersecting at a corner.

7. The orthopedic implant according to claim 1 wherein the soft tissue attachment pad comprises first and second opposing terminal ends, and at least a portion of the suture accepting bore is disposed on one of the first and second opposing terminal ends.

8. A prosthetic comprising:
   a head portion having an articulating surface;
   a base member having a bone engaging surface defining a taper, said bone engaging surface coupled directly to said head portion to form a complete implantable prosthetic, said base member defining an outer fixation surface, said base member having a locking mechanism including a first fastener accepting bore defined in the outer fixation surface; and
   a selectable attachable soft tissue attachment pad comprising a plate and a separate porous metal pad attached thereto, said plate defining a notched recess disposed between opposing proximal and distal flanges and configured to accept said porous metal pad, said attachable soft tissue attachment pad defining a suture accepting bore and a second fastener accepting bore configured for alignment with the first fastener accepting bore, wherein said attachable soft tissue attachment pad couples to the outer fixation surface, wherein said locking mechanism is configured to prevent movement of the soft tissue attachment pad with respect to the base member.

9. The prosthetic according to claim 8 wherein said locking mechanism further comprises a threaded fastener disposed through the first and second fastener accepting bores, coupling the soft tissue attachment pad to the base member.

10. The prosthetic according to claim 8 wherein the soft tissue attachment pad comprises a planar plate having a planar fixation coupling surface.

11. The prosthetic according to claim 10 wherein the planar fixation coupling surface is configured to be coupled to a planar surface on the base member.

12. The prosthetic according to claim 10 further comprising an intermediary member, said intermediary member defining a fastener accepting aperture therethrough, and having an intermediary member planar bearing surface configured to interface with the planar fixation surface and an intermediary member curved bearing surface configured to interface with a base member convex surface.

13. The prosthetic according to claim 10 wherein the planar fixation coupling surface defines the second fastener accepting bore.

14. The prosthetic according to claim 10 wherein the general planar plate is circular.

15. The prosthetic according to claim 14 wherein the plate defines a central portion having the porous metal soft tissue attachment pad.

16. The prosthetic according to claim 15 wherein the plate defines a circular rim.

17. The prosthetic according to claim 16 wherein the circular rim defines a plurality of suture accepting bores.

18. The prosthetic according to claim 8 comprising a plurality of fastener accepting bores defined in the outer fixation surface.

19. The prosthetic according to claim 8 wherein the soft tissue attachment pad comprises first and second terminal ends, and at least a portion of the suture accepting bore is disposed on one of the first and second opposing terminal ends.

20. A modular humeral prosthetic comprising:
a head portion having an articulating surface;
a base member coupled directly to the head portion, the base member including an outer fixation surface defining a plurality of fastener accepting bores;
at least one soft tissue attachment pad comprising:
a curved plate having first and second opposing major surfaces, the first major surface defining a coupling surface configured for mating engagement with the outer fixation surface of the base member, the second major surface defining a notched recess disposed between opposing proximal and distal flanges and configured to accept a porous metal pad;
at least one fastener accepting aperture defined through the curved plate and the porous metal material configured for alignment with one of the plurality of fastener accepting bores defined in the base member, wherein the soft tissue attachment pad defines at least one suture accepting bore; and
a fastener for joining the coupling surface of the curved plate to the outer fixation surface of the base member, the fastener configured to prevent movement of the soft tissue attachment pad with respect to the base member.

* * * * *